United States Patent
Oliver et al.

(10) Patent No.: US 7,766,794 B2
(45) Date of Patent: Aug. 3, 2010

(54) MOBILE EXERCISE ENHANCEMENT WITH VIRTUAL COMPETITION

(75) Inventors: Nuria Oliver, Redmond, WA (US); Rodrigo de Oliveira, Campinas (BR)

(73) Assignee: Microsoft Corporation, Redmond, WA (US)

(*) Notice: Subject to any disclaimer, the term of this patent is extended or adjusted under 35 U.S.C. 154(b) by 0 days.

(21) Appl. No.: 11/934,522

(22) Filed: Nov. 2, 2007

(65) Prior Publication Data
US 2009/0118100 A1  May 7, 2009

(51) Int. Cl.
*A63B 71/00* (2006.01)
*G06F 19/00* (2006.01)

(52) U.S. Cl. .............................................. 482/8; 700/92

(58) Field of Classification Search ...................... 482/1, 482/3, 8, 9; 463/1, 7, 23, 31; 273/441, 444; 386/124; 348/157; 701/207, 208; 700/91, 700/92
See application file for complete search history.

(56) References Cited

U.S. PATENT DOCUMENTS

| | | | | |
|---|---|---|---|---|
| 4,311,310 A | * | 1/1982 | Dankman et al. | ........... 273/109 |
| 4,548,289 A | * | 10/1985 | Mechling | ................... 600/587 |
| 4,911,427 A | * | 3/1990 | Matsumoto et al. | ............ 482/9 |
| 5,566,951 A | * | 10/1996 | Dart et al. | ................... 273/358 |
| 5,795,301 A | * | 8/1998 | Yasukawa et al. | ........... 600/500 |
| 6,013,008 A | * | 1/2000 | Fukushima | ..................... 482/8 |
| 6,213,872 B1 | * | 4/2001 | Harada et al. | ................... 463/7 |
| 6,230,047 B1 | | 5/2001 | McHugh | |
| 6,436,058 B1 | * | 8/2002 | Krahner et al. | .............. 600/587 |
| 6,527,674 B1 | | 3/2003 | Clem | |
| 6,634,992 B1 | * | 10/2003 | Ogawa | ........................... 482/8 |
| 6,648,798 B2 | * | 11/2003 | Yoo | ............................... 482/8 |
| 6,659,916 B1 | | 12/2003 | Shea | |
| 6,746,370 B1 | * | 6/2004 | Fleming et al. | ................ 482/1 |

(Continued)

FOREIGN PATENT DOCUMENTS

WO    WO2007017739 A2    2/2007

(Continued)

OTHER PUBLICATIONS

Oliver, et al., "Enhancing Exercise Performance through Real-time Physiological Monitoring and Music: A User Study", pp. 10.

(Continued)

*Primary Examiner*—Loan H Thanh
*Assistant Examiner*—Sundhara M Ganesan

(57) ABSTRACT

A glanceable interface presented by a computing device to a user while the user engages in physical exercise can provide information regarding exercise-related data within the context of the user's exercise-oriented goals. In particular, the glanceable interface can display the difference between a user's current exercise level and a target level, optionally with instructions how to reach the target level. Once the target level is reached, the glanceable display can provide raw exercise-related data to the user. In addition, virtual competition can be based on a target-achievement-score that is based on the amount of time, and the accuracy with which, a competitor maintains their exercise level within a target exercise level zone. Competitors can be automatically selected based on the closeness of their target-achievement-scores to the user's target-achievement-score, so long as at least one competitor has a higher target-achievement-score than the user so as to further motivate the user.

20 Claims, 6 Drawing Sheets

U.S. PATENT DOCUMENTS

| | | | |
|---|---|---|---|
| 6,786,848 B2 * | 9/2004 | Yamashita et al. | 482/8 |
| 6,796,927 B2 * | 9/2004 | Toyama | 482/8 |
| 6,824,499 B2 | 11/2004 | Wu et al. | |
| 6,852,068 B2 * | 2/2005 | Ogawa | 482/8 |
| 6,881,176 B2 * | 4/2005 | Oishi et al. | 482/8 |
| 6,941,238 B2 * | 9/2005 | Tanifuji | 702/127 |
| 7,063,643 B2 * | 6/2006 | Arai | 482/8 |
| 7,063,644 B2 * | 6/2006 | Albert et al. | 482/8 |
| 7,072,789 B2 * | 7/2006 | Vock et al. | 702/141 |
| 7,097,588 B2 * | 8/2006 | Watterson et al. | 482/8 |
| 7,217,224 B2 * | 5/2007 | Thomas | 482/8 |
| 2001/0049322 A1 * | 12/2001 | Watanabe et al. | 482/8 |
| 2002/0022551 A1 * | 2/2002 | Watterson et al. | 482/8 |
| 2003/0022140 A1 * | 1/2003 | Chang | 434/247 |
| 2003/0064860 A1 * | 4/2003 | Yamashita et al. | 482/8 |
| 2003/0078138 A1 * | 4/2003 | Toyama | 482/8 |
| 2003/0134714 A1 * | 7/2003 | Oishi et al. | 482/6 |
| 2003/0171190 A1 * | 9/2003 | Rice | 482/57 |
| 2004/0063481 A1 * | 4/2004 | Wang | 463/8 |
| 2004/0229729 A1 * | 11/2004 | Albert et al. | 482/8 |
| 2004/0242294 A1 * | 12/2004 | Shiozawa | 463/9 |
| 2005/0124463 A1 * | 6/2005 | Yeo et al. | 482/8 |
| 2005/0196737 A1 * | 9/2005 | Mann | 434/247 |
| 2005/0209050 A1 | 9/2005 | Bartels | |
| 2005/0209052 A1 * | 9/2005 | Ashby et al. | 482/9 |
| 2005/0233861 A1 * | 10/2005 | Hickman et al. | 482/8 |
| 2005/0288154 A1 * | 12/2005 | Lee et al. | 482/3 |
| 2006/0040793 A1 * | 2/2006 | Martens | 482/8 |
| 2006/0057549 A1 * | 3/2006 | Prinzel et al. | 434/247 |
| 2006/0099556 A1 * | 5/2006 | Yeo et al. | 434/247 |
| 2006/0107822 A1 | 5/2006 | Bowen | |
| 2006/0111621 A1 | 5/2006 | Coppi et al. | |
| 2006/0169125 A1 | 8/2006 | Ashkenazi et al. | |
| 2006/0217231 A1 * | 9/2006 | Parks et al. | 482/3 |
| 2006/0229163 A1 * | 10/2006 | Waters | 482/8 |
| 2006/0240947 A1 * | 10/2006 | Qu | 482/1 |
| 2006/0243120 A1 | 11/2006 | Takai et al. | |
| 2007/0042868 A1 * | 2/2007 | Fisher et al. | 482/8 |
| 2007/0044641 A1 | 3/2007 | McKinney et al. | |
| 2007/0049462 A1 * | 3/2007 | Asukai et al. | 482/8 |
| 2007/0074618 A1 | 4/2007 | Vergo | |
| 2007/0113725 A1 | 5/2007 | Oliver et al. | |
| 2007/0232453 A1 * | 10/2007 | Hanoun | 482/7 |
| 2007/0260482 A1 * | 11/2007 | Nurmela et al. | 705/2 |
| 2007/0287596 A1 * | 12/2007 | Case et al. | 482/8 |
| 2008/0096726 A1 * | 4/2008 | Riley et al. | 482/8 |
| 2008/0109158 A1 * | 5/2008 | Huhtala et al. | 701/208 |
| 2008/0139307 A1 * | 6/2008 | Ueshima et al. | 463/31 |
| 2008/0200312 A1 * | 8/2008 | Tagliabue | 482/9 |
| 2008/0269017 A1 * | 10/2008 | Ungari | 482/4 |
| 2009/0069089 A1 * | 3/2009 | Piccioni et al. | 463/42 |

FOREIGN PATENT DOCUMENTS

| | | |
|---|---|---|
| WO | WO2007044537 A2 | 4/2007 |
| WO | WO2007022421 A2 | 10/2007 |

OTHER PUBLICATIONS

Oliver, et al., "MPTrain: A Mobile, Music and Physiology Based Personal Trainer", 2006, ACM, pp. 8.

"Triple Beat", retrieved at<<http://research.microsoft.com/nuria/tripleBeat/TripleBeat.htm>>, Aug. 23, 2007, pp. 1.

"Index of /Sashtml/stat", retrieved at <<http://v8doc.sas.com/sashtml/stat/>>, pp. 4.

Mueller, et al, "Jogging over a Distance", 2007, ACM, pp. 1989-1994.

Flegal, et al., "Overweight and Obesity", 1998, vol. 22, No. 1, pp. 39-47.

Diwakar, et al., "Personal Digital Exercise tRainer for Managing, Monitoring and Recording the Exercise", 2005, IEEE, pp. 3720-3723.

Elliott, et al., "PersonalSoundtrack: Context-Aware Playlists that Adapt to User Pace", 2006, ACM, pp. 736-741.

Makikawa, et al., "Portable Jogging Monitor Device and its Application for Health Management", 2003, IEEE, pp. 40-41.

"Preventing Obesity and Chronic Diseases Through Good Nutrition and Physical Activity", US Department of Health and Human Services, pp. 2.

Goodman, et al., "Seeing Fit; Visualizing Physical Activity in Context", 2006, ACM, pp. 797-802.

Um, "The Effect of a Regular Exercise on Mental Health on Aged People", 2004, IEEE, pp. 284-286.

Dietz, "The Global Epidemic of Obesity", pp.-6.

Shin et al., "The Power Spectral Analysis of Heart Rate Variability During Exercise", 1993, IEEE, pp. 786-787.

Abowd et al., "The Smart Phone: A first Platform for Pervasive Computing", 2005, IEEE, pp. 18-19.

Mathew, "Using the Environment as an Interactive Interface to Motivate Positive Behavior Change in a Subway Station", 2005, ACM, pp.-4.

Booth, et al., "Waging war on a physical inactivity: using modern molecular ammunition against an ancient enemy", 2002, vol. 93, Issue-1, pp. 6.

Arroyo, et al., "Waterbot: Exploring Feedback and Persuasive Technique at the Sink", 2005, ACM, pp. 9.

"A Little Video for Everyone. The new iPod nano", retrieved at <<http://www.apple.com/itunes/>>, pp. 1.

Wijnalda, et al., "A Personalized Music System for Motivation in Sport Performance", 2005, IEEE, pp. 26-32.

Hartnett, et al., "A Responsive and Persuasive Audio Device to Stimulate Exercise and Fitness in Children", 2006, ACM, pp. 1837-1842.

Kwak, et al., "An Integrated System for Body Shape Analysis and Physical Fitness Test- HIMS", 2005, IEEE, pp. 3742-3745.

Jang, et al., "Automated Individual Prescription of Exercise with an XML-Based Expert System", 2005, IEEE, pp. 882-885.

Gockley, et al., "AVIVA: A Health and Fitness Monitor for Young Women", 2006, ACM, pp. 1819-1824.

Buttussi, et al., "Bringing Mobile Guides and Fitness Activities Together: a Solution Based on an Embodied Virtual Trainer", 2006, ACM, pp. 8.

Toscos, et al., "Chick Clique: Persuasive Technology to Motivete Teenage Girls to Exercise", 2006, ACM, pp. 1873-1878.

Andrew, et al., "Context to Make You More Aware", 2007, IEEE, pp. 6.

Wang, et al., "Design of a Web-Based Health Promotion system and its Practical Implementation for Cycle Engrometer Exercise", 2004, IEEE, pp. 3330-3333.

Consolvo, et al., Design Requirement for Technologies that Encourage Physical Activity, 2006, ACM, pp. 457-466.

Linder, et al., "Detecting Exercise Induced Stress using the Photoplethysmogram", 2006, IEEE, pp. 5109-5112.

Biehl, et al., "DJogger: A Mobile Dynamic Music Device", 2006, ACM, pp. 556-561.

Vorderer, et al., "Explaining the Enjoyment of Playing Video Games: The Role of Competition", pp. 1-9.

Mokka, et al., "Fitness Computer Game with a Bodily User Interface", pp. 1-3.

Ching, et al., "Fitness Monitor System", 2003, IEEE, pp. 5.

Cheok, et al., Human Pacman; A mobile Wide-Area Entertainment System Based on Physiacl Social and Ubiquitous Computing:, Dec. 12, 2003, pp. 1-24.

Asselin, et al., "Implementation and Evaluation of the Personal Wellness Coach", 2007, IEEE, pp. 1.

\* cited by examiner

MOBILE EXERCISE ENHANCEMENT WITH VIRTUAL COMPETITION

BACKGROUND

Well known correlations exist between the amount of physical exercise an individual engages in and that individual's mental and physical health. Statistical data indicates that upwards of two million people die each year from causes that are attributable to a lack of sufficient physical exercise. Additionally, well known correlations exist between an individual's level of motivation to remain physically active and the amount of physical exercise they actually perform. Thus, devices that aid in maintaining or increasing an individual's motivation to engage in physical exercise are often used in conjunction with an individual's exercise regiment.

Music can act as a means of motivation to continue physical exercise, and it can aid the user in ignoring any physical discomfort the user may be experiencing while they exercise. Consequently, portable music devices have often been incorporated by users into their exercise regiment. While such portable music devices have traditionally been smaller versions of home entertainment devices, such as radios, cassette players and compact disk players, modern portable music devices are increasingly digital computing devices designed to decode music, or other audio/visual entertainment based on digital formats. Such devices often include capabilities beyond merely decoding audio/visual content, such as the ability to execute other computer-readable instructions, display photographs, play games or engage in wireless communication, including cellular telephony.

Because modern portable music devices can execute other computer-readable instructions, the motivation a user receives from the music they are listening to can be tailored to aid the user in achieving predetermined exercise goals. For example, as described in co-pending U.S. Patent Application No. 2007/00113725A1, which is assigned to the assignee of the present application, a user's heart rate during exercise can be monitored and, if the user's heart rate deviates from a target heart rate, the music played by the portable music device can be selected such that it either encourages the user to increase or decrease their exercise effort so as to reach their target heart rate.

SUMMARY

Modern portable music devices or, more generally, any portable computing device that can decode and play back audio and visual entertainment, traditionally comprises a display or other mechanism of visual feedback. Such a visual feedback mechanism can be utilized, either by itself, or in conjunction with auditory mechanisms, such as the selection of music, to further a user's motivation to both engage in physical exercise and to do so in a manner that will optimally achieve the user's exercise goals.

In one embodiment, the visual feedback mechanism can provide a glanceable interface that incorporates shapes, colors, iconic signs and the like to provide goal-related information to a user in a glanceable manner. In particular, the glanceable interface can display the deviation between a user's target level, as determined by the user's exercise goals, and the user's current level. The glanceable interface can also display the actions required to enable the user to reach their target level. For example, in one embodiment, a target heart rate can be determined based on the user's exercise goals using well-known formulae. The difference between the user's current heart rate, as determined, for example, by a heart rate monitor, and the user's target heart rate, can be prominently displayed on the glanceable interface. Similarly, the action the user needs to take, such as to increase or decrease their heart-rate can, likewise, be displayed on the glanceable interface. In such a manner, the user is not presented with raw data, such as their current heart rate, but rather is presented with meaningful information regarding the achievement of the user's exercise goals.

In another embodiment, once the user has achieved their target level, the glanceable interface can display raw exercise-related data, such as heart rate. Consequently, as the user approached their target level, the glanceable interface could, according to this further embodiment, transition from displaying the difference between the user's current level and their target level, to a display of raw exercise-related data once the user reached their target level. Such a transition can likewise comprise a color change, an iconic symbol change, and other changes to communicate information to the user in a glanceable manner.

In a further embodiment, a virtual competition can be established and maintained, at least in part, by the portable computing device, and can be presented to the user through auditory or visual means. The virtual competition can be based on the ability of the competitors to maintain a target exercise level that was individually selected for each of the competitors. In such a manner, the virtual competition encourages productive and goal-oriented exercise, as opposed to simply rewarding raw strength or speed.

In a still further embodiment, the virtual competition can be based on a target-achievement-score designed to provide an objective measure of how well each competitor is exercising within a target range determined by each competitor's pre-determined exercise goals. For example, in one embodiment, a target heart rate for each competitor can be determined based on each competitors' exercise goals and the target-achievement-score can be proportional to the amount of time each competitor's heart rate stayed within the target range and can also be proportional to an accuracy function that can quantify how close the competitor's heart rate is to a target heart rate at a point in time.

In a yet further embodiment, information regarding potential competitors' exercise sessions can be maintained, either locally or on a remote device accessible by the portable computing device, and can be used to inform the selection of appropriate competitors for a given user. While, in one embodiment, the user can simply be presented the relevant information and can be enabled to select their own competitors, in another embodiment, the selection of competitors can occur automatically based on the potential competitors' whose target-achievement-scores are closest to the user. Additionally, in a further embodiment, the automatic selection of competitors can ensure that at least one competitor is selected whose target-achievement-score is expected to be greater than the user's so as to leverage the user's competitive spirit, and thereby provide greater motivation to the user.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Additional features and advantages will be made apparent from the following detailed description that proceeds with reference to the accompanying drawings.

DESCRIPTION OF THE DRAWINGS

The following detailed description may be best understood when taken in conjunction with the accompanying drawings, of which.

DETAILED DESCRIPTION

Figure 1:
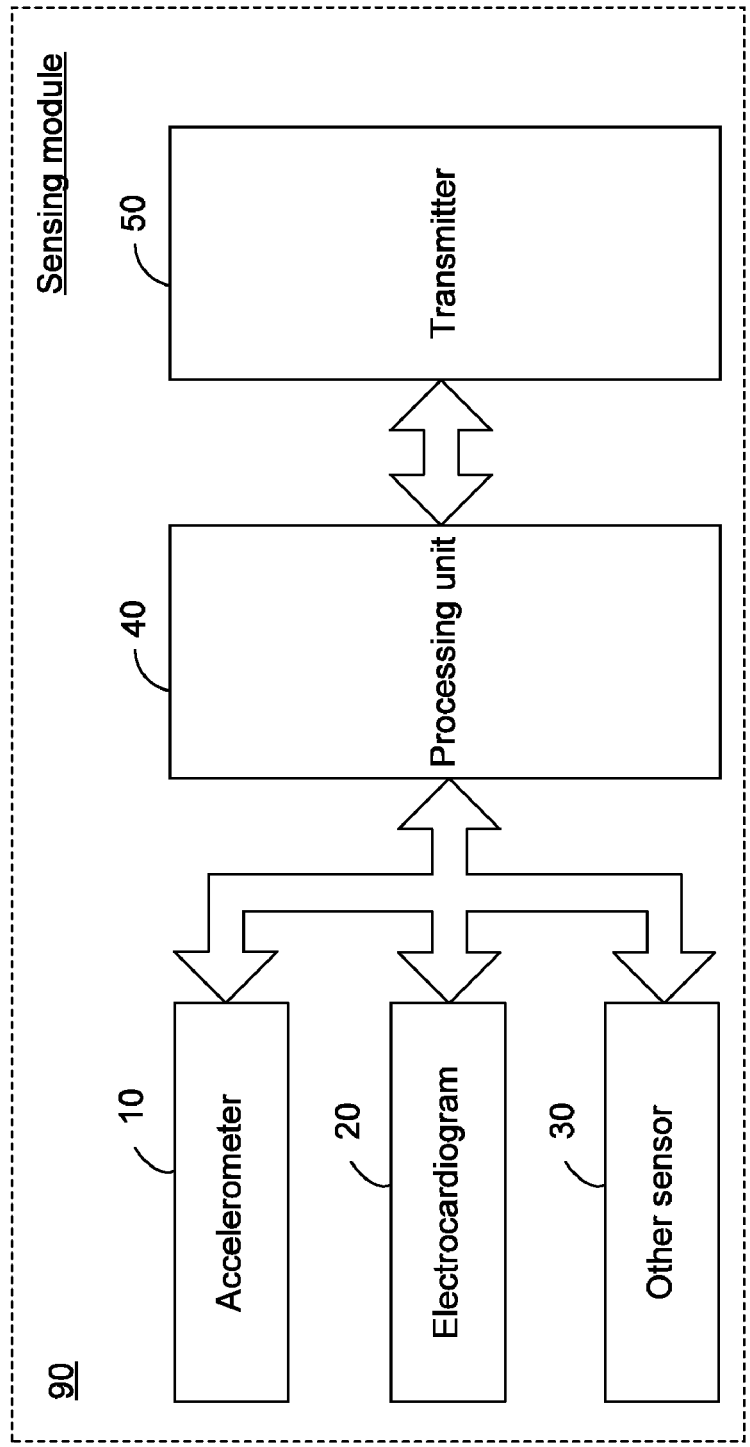
FIG. 1 is a diagram of an exemplary sensing module.

The following description relates to the provision of virtual competition and a glanceable interface via a portable computing device so as to increase a user's motivation to engage in physical exercise and achieve target exercise levels appropriate for that user's stated exercise goals. The glanceable interface can provide users with information regarding the difference between their current exercise level and an appropriate target exercise level, and can provide users with simple instructions to guide the user to reaching the target exercise level, thereby enabling the user to quickly ascertain how to reach their target exercise level. The virtual competition can be based on a target-achievement-score that can objectively measure each competitor's maintenance of a target exercise level appropriate for each competitor's stated exercise goals. The virtual competition can include, when automatically selected, at least one competitor whose target-achievement-score is expected to be greater than the user's, thereby relying on the user's competitive spirit to further motivate them.

The techniques described herein focus on the design, implementation and usage of the glanceable interface and virtual competition to motivate a user to perform physical exercise at an appropriate intensity level. However, the techniques described herein are not limited to the use of a glanceable interface or virtual competition to the exclusion of other motivating mechanisms. To the contrary, either or both the glanceable interface and the virtual competition can be used with other motivating mechanisms. For example, co-pending United States Application No. 2007/00113725A1, which is assigned to the assignee of the present application, and whose contents are herein incorporated by reference in their entirety for all that they may teach or suggest, describes a mechanism by which the music played by a portable computing device to which the user is listening during an exercise session is selected to instinctively guide the user to an appropriate level, such as by selecting songs with a faster beat when the user needs to increase their exercise intensity. Such a music-selection mechanism can be used in conjunction with either or both the glanceable interface and the virtual competition to further motivate the user to exercise at an appropriate level. Consequently, while the descriptions below will focus on the glanceable interface and the virtual competition mechanisms, nothing in the below descriptions is intended to limit the motivation of a user to only those mechanisms.

Although not required, the description below will be in the general context of instructions being executed by a device having computational abilities. Such "computing devices" include both traditional computers and consumer-electronic devices having computational abilities, such as those provided by a central processing unit. Thus, the description below will be in the general context of "computer-executable instructions," such as program modules, that are capable of being executed by a such a "computing device." More specifically, the description will reference acts and symbolic representations of operations that are performed by one or more computing devices or peripherals, unless indicated otherwise. As such, it will be understood that such acts and operations, which are at times referred to as being computer-executed, include the manipulation by a processing unit of electrical signals representing data in a structured form. This manipulation transforms the data or maintains it at locations in memory, which reconfigures or otherwise alters the operation of the computing device or peripherals in a manner well understood by those skilled in the art. The data structures where data is maintained are physical locations that have particular properties defined by the format of the data.

Generally, program modules include routines, programs, objects, components, data structures, and the like that perform particular tasks or implement particular abstract data types. Moreover, those skilled in the art will appreciate that the computing devices need not be limited to conventional personal computers and conventional personal electronics devices, and can include other devices capable of computation, including hand-held devices, multi-processor systems, other microprocessor based or programmable consumer electronics, network PCs, minicomputers, mainframe computers, and the like. Similarly, the computing devices need not be limited to a stand-alone device, as the mechanisms may also be practiced in distributed computing environments where tasks are performed by remote processing devices that are linked through a communications network. In a distributed computing environment, program modules may be located in both local and remote memory storage devices.

With reference to FIG. 1, an exemplary sensing module 90 is illustrated, providing context for the descriptions below. Exemplary sensing module 90 includes various sensors 10, 20 and 30, though, in an alternative embodiment, each of the sensors 10, 20 and 30 could be encapsulated within their own sensing module. The sensors 10, 20 and 30 can collect information pertinent to a user's physical exercise, including heart rate information, activity information and the like. Thus, the exemplary sensing module 90 includes an electrocardiogram 90 for measuring a user's heart rate, a 3-axis accelerometer 10, which can be used to measure a user's pace, the distance a user has traveled, the type of movement or similar information, and another sensor 30 which can measure other information pertinent to the user's physical exercise, including, but not limited to the user's location, external and internal temperature, dehydration levels and the like.

Each of the sensors 10, 20 and 30 can be communicationally coupled, either through a direct physical connection, or through a wireless communication connection, to a processing unit 40. The processing unit 40 can be a general-purpose processing unit, or it can be a processing unit specifically designed for functionality limited to, for example, the storage and transmission of the information received from the sensors 10, 20 and 30. In one embodiment, the processing unit 40 can repackage information received from the sensors 10, 20 and 30 into a format capable of being transmitted to a receiver external to the sensing module 90. Such transmission can be accomplished by means of a transmitter 50, which can be a wireless transmitter conforming to either short-range or long-range wireless communication standards, or it can be a wire-based transmitter. In one embodiment, the transmitter 50 can implement standard short-range wireless communications, such as would be supported by portable computing devices, including digital music players, cellular telephones, personal digital assistants, and the like.

Figure 2:
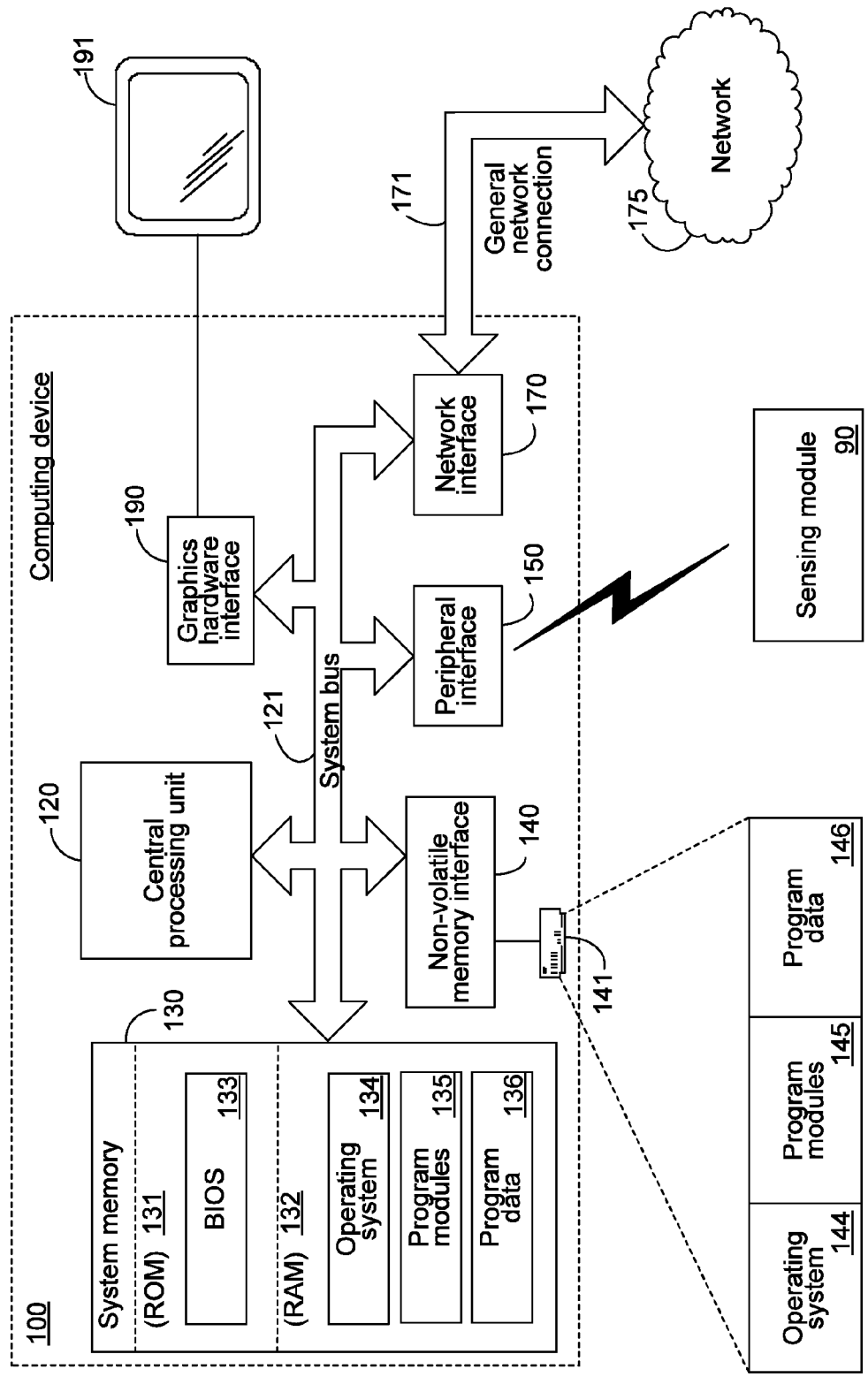
FIG. 2 is a block diagram of an exemplary computing device.

Turning to FIG. 2, an exemplary portable computing device 100 is illustrated. As indicated previously, the term "computing device," as used herein, includes consumer entertainment devices, such as portable video game consoles, portable digital video recorders and players and portable digital music recorders and players. The term "computing device" likewise extends to more traditional computing devices, such as laptop computers, palmtop computers, wearable computing devices, personal digital assistants, cellular telephones or cellular telephony devices, and hybrids thereof.

The exemplary portable computing device 100 can include, but is not limited to, one or more central processing units (CPUs) 120, a system memory 130, and a system bus 121 that couples various system components including the system memory to the processing unit 120. The system bus 121 may be any of several types of bus structures including a memory bus or memory controller, a peripheral bus, and a local bus using any of a variety of bus architectures. The computing device 100 can include graphics hardware, including, but not limited to, a graphics hardware interface 190 and a display device 191, including, for example, Liquid Crystal Display (LCD) devices that are physically part of the computing device 100.

The computing device 100 also typically includes computer readable media, which can include any available media that can be accessed by computing device 100 and includes both volatile and nonvolatile media and removable and non-removable media. By way of example, and not limitation, computer readable media may comprise computer storage media, communication media or combinations thereof. Computer storage media includes media implemented in any method or technology for storage of information such as computer readable instructions, data structures, program modules or other data. Communication media typically embodies computer readable instructions, data structures, program modules or other data in a modulated data signal such as a carrier wave or other transport mechanism and includes any information delivery media.

The system memory 130 includes computer storage media in the form of volatile and/or nonvolatile memory such as read only memory (ROM) 131 and random access memory (RAM) 132. A basic input/output system 133 (BIOS), containing the basic routines that help to transfer information between elements within computing device 100, such as during start-up, is typically stored in ROM 131. RAM 132 typically contains data and/or program modules that are immediately accessible to and/or presently being operated on by processing unit 120. By way of example, and not limitation, FIG. 2 illustrates operating system 134, other program modules 135, and program data 136. Program modules 135 can include programs for recording and playing back audio and visual content and such content can be considered part of the program data 146.

The computing device 100 may also include other removable/non-removable, volatile/nonvolatile computer storage media. By way of example only, FIG. 2 illustrates a Solid-State Drive (SSD) 141 that reads from or writes to nonvolatile transistor-based media. Other removable/non-removable, volatile/nonvolatile computer storage media that can be used with the exemplary computing device include, but are not limited to, hard disk drives, magnetic tape cassettes, flash memory cards, digital versatile disks, digital video tape, solid state RAM, solid state ROM, and the like. The SSD 141 is typically connected to the system bus 121 through an interface such as the non-volatile memory interface 140.

The drives and their associated computer storage media discussed above and illustrated in FIG. 2, provide storage of computer readable instructions, data structures, program modules and other data for the computing device 100. In FIG. 2, for example, SSD 141 is illustrated as storing operating system 144, other program modules 145, and program data 146. Note that these components can either be the same as or different from operating system 134, other program modules 135 and program data 136. Operating system 144, other program modules 145 and program data 146 are given different numbers here to illustrate that, at a minimum, they are different copies.

The computing device 100 may operate in a networked environment using logical connections to one or more remote computing or communication devices. The computing device 100 is not limited to any particular network or networking protocols. Thus, the network connection depicted is a general network connection 171 that can represent a connection to a local area network (LAN), a wide area network (WAN) or other networks, each represented by the general network 175. For example, the general network connection 171 and network 175 can represent a cellular connection if the computing device 100 was a cellular telephone or personal digital assistant, or they could represent a wireless network if the computing device 100 was a portable audio or video player or a palmtop or laptop computing device. The computing device 100 is connected to the general network connection 171 through a network interface or adapter 170 which is, in turn, connected to the system bus 121. In a networked environment, program modules depicted relative to the computing device 100, or portions or peripherals thereof, may be stored in the memory of one or more other computing devices that are communicatively coupled to the computing device 100 through the general network connection 171. It will be appreciated that the network connections shown are exemplary and other means of establishing a communications link between computing devices may be used.

In addition to the wireless, or wire-based, general network connection 171, the computing device 100 can further comprise a peripheral interface 150, connected to the system bus 121, for enabling communications between the computing device and peripherals, such as the sensing module 90 illustrated in detail in FIG. 1. In one embodiment, for ease of use in an exercise session, the peripheral interface 150 can support wireless peripheral-oriented protocols that are compatible with the transmitted 50 of the sensing module 90. In such a manner one or more sensing modules 90 can be positioned in accordance with the requirements of the sensors 10, 20 and 30, and can communicationally connect to the computing device 100 via the transmitter 50 and the peripheral interface 150. For example, a sensing module 90 comprising an electrocardiogram 20 can be connected to the user's chest and can wirelessly communicate with the computing device 100, which can be carried by the user or placed in their pocket. In an alternative embodiment, however, the peripheral interface 150 can support wire-based peripheral communications.

Figure 3:
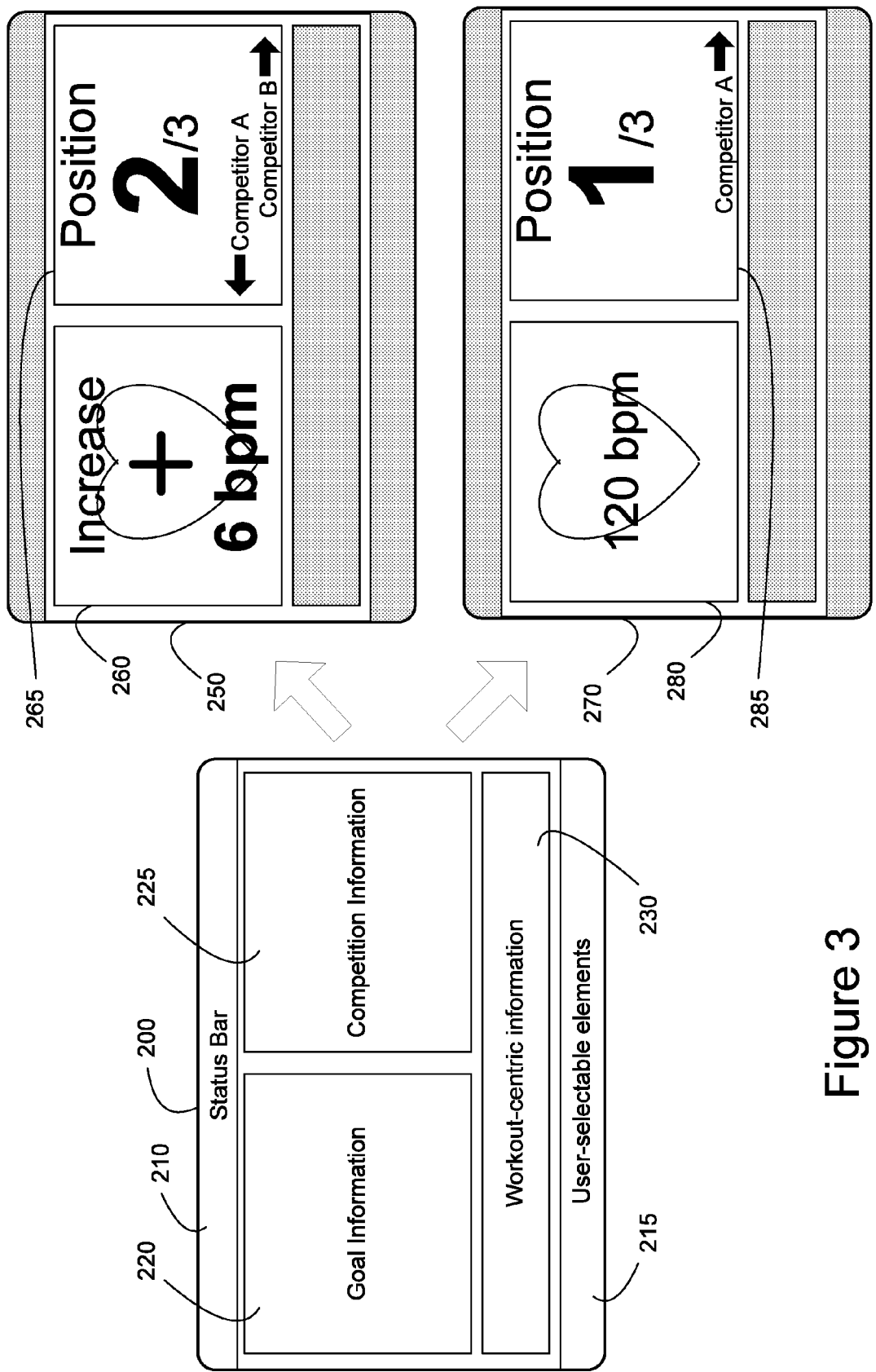
FIG. 3 is an example of a glanceable interface.

The data obtained by the sensors 10, 20 and 30 of the sensing module 90 can be communicated to the computing device 100 where it can be processed by the CPU 120 and can be meaningfully presented to the user via, for example, the display 191, as driven by the graphics hardware interface 190. In one embodiment, such a meaningful presentation can comprise the presentation of a glanceable interface to the user by the display 191. Turning to FIG. 3, an exemplary structure for a glanceable interface 200 is illustrated. In the embodiment illustrated, the glanceable interface 200 can comprise a prominent display of goal information 220 and competition information 225 and can secondarily display workout-centric information 230, user selectable elements 215 and a status bar 210. The glanceable interface 200 is intended to convey information to the user under circumstances typically present during an exercise session. Thus, significant information can be presented in a large and uncluttered manner in the center of the glanceable interface 200, while secondary information, that the user may desire only on an intermittent basis, is presented in smaller, less-centered areas.

Among the information that the user may only intermittently desire during their exercise session can be status information that can be displayed in the status bar 210. Such status information can include information regarding the battery, such as the remaining battery power, of the computing device 100 or the sensing module 90, information regarding the signal strength of the sensing module 90, or a wireless or cellular network, and identification information, such as the name of the program providing the glanceable interface 200. Other information that the user may only intermittently desire during their exercise session can be workout-centric information displayed in area 230, which can include information such as a timer, or countdown timer, of the exercise session, an estimation of the number of calories burned during the exercise session, an estimation of the distance traveled, or other cumulative measure of the exercise session, and can also include information regarding any entertainment being presented by the computing device 100 to the user, such as the name and duration of a song that the computing device is currently playing.

In some cases, space-limited computing devices, such as cellular telephones, personal digital assistants, and palmtop computing devices can provide for multi-use interface elements, such as buttons that are located proximately to the display 191. Traditionally, the functionality assigned to such multi-use interface elements can be displayed to the user via the user-selectable elements section 215, with each multi-use interface element having an associated label displayed proximately to it within section 215. Alternatively, the user-selectable elements sections 215 can simply display user options and settings that can be selected through conventional data entry mechanisms.

Among the primary information that can be presented to the user via the glanceable interface 200 can be information obtained from the sensing module 90. In one embodiment, such information can be presented to the user within the context of the user's exercise goals. For example, using well-known formulae, a user's target heart rate can be determined based on the user's personal information, such as the user's age, and on the user's exercise goals, such as the improvement of cardiovascular strength, or the burning of additional calories. One such formula is known as the Karyonen formula, which states that a user's target heart rate when exercising is equal to that user's resting heart rate plus a percentage of the users "reserve" heart rate, which is the difference between the user's maximum heart rate and their resting heart rate. While a user's resting heart rate can be empirically determined by measuring their heart rate while the user is at rest, a user's maximum heart rate, rather than being determined empirically, can be simply the difference between the user's age (in years) and the number 220. The percentage of the user's reserve heart rate that is used in the Karyonen formula can range from 50% to 100%, depending on the exercise goals of the user. For example, a user whose goal is to improve their cardiovascular strength should exercise such that their target heart rate is given by the Karyonen formula using a percentage value between 70% and 80%. These upper and lower bounds for the user's target heart rate can define a target heart rate zone.

Once such a target heart rate, and target heart rate zone have been determined, the data collected from, for example, the electrocardiogram 20 can be presented to the user via the glanceable interface 200 in a format that references the user's target heart rate and provides context for the electrocardiogram data. Specifically, the user can be provided with raw data when the data is already within the user's target range. If the measured data is not within the user's target range, the user can, instead, be presented with an indication of the deviation between the user's target range and the current measured data.

Glanceable interfaces 250 and 270 illustrate an aspect of the above-described embodiments. Specifically, the goal information area 220 of the glanceable interface 200 can display either the difference between the user's current data and the user's target range, optionally together with an indication of how to reach the target range, or it can display the user's current data if such data is already within the user's target range. Thus, as illustrated by glanceable interface 250, the goal information area 260 can indicate that the user's current heart rate is six beats-per-minute below the user's target heart rate, such as would have been determined from the user's exercise goals. Consequently, the goal information area 260 can instruct the user to increase their current heart rate by six beats-per-minute so as to reach their target heart rate. Once the user's current data reaches the user's target range, such as in the case illustrated by glanceable interface 270, the goal information area 280 can display the user's data directly, such as the number of beats-per-minute of the user's heart.

Other aspects of the above-described embodiments, which are not easily illustrated by the glanceable interfaces 250 and 270 include the use of color, animation, icons, symbols or other easy-to-discern mechanisms to convey the above-described information. For example, while the user's current data indicates that the user is not within their target range, a color, such as red, can dominate the presentation of information in area 260. Once a user's current data indicates that the user has achieved their target range, a different color, such as green, can dominate the presentation of information in area 280. In such a case, the user would need to perceive nothing more than the color to, at a minimum, determine whether they had achieved their target range. Similarly, easy-to-distinguish symbols, such as the "plus" sign, "minus" sign, or even the lack of any such signs, can be used to again provide glanceable instructions to the user.

Figure 4:
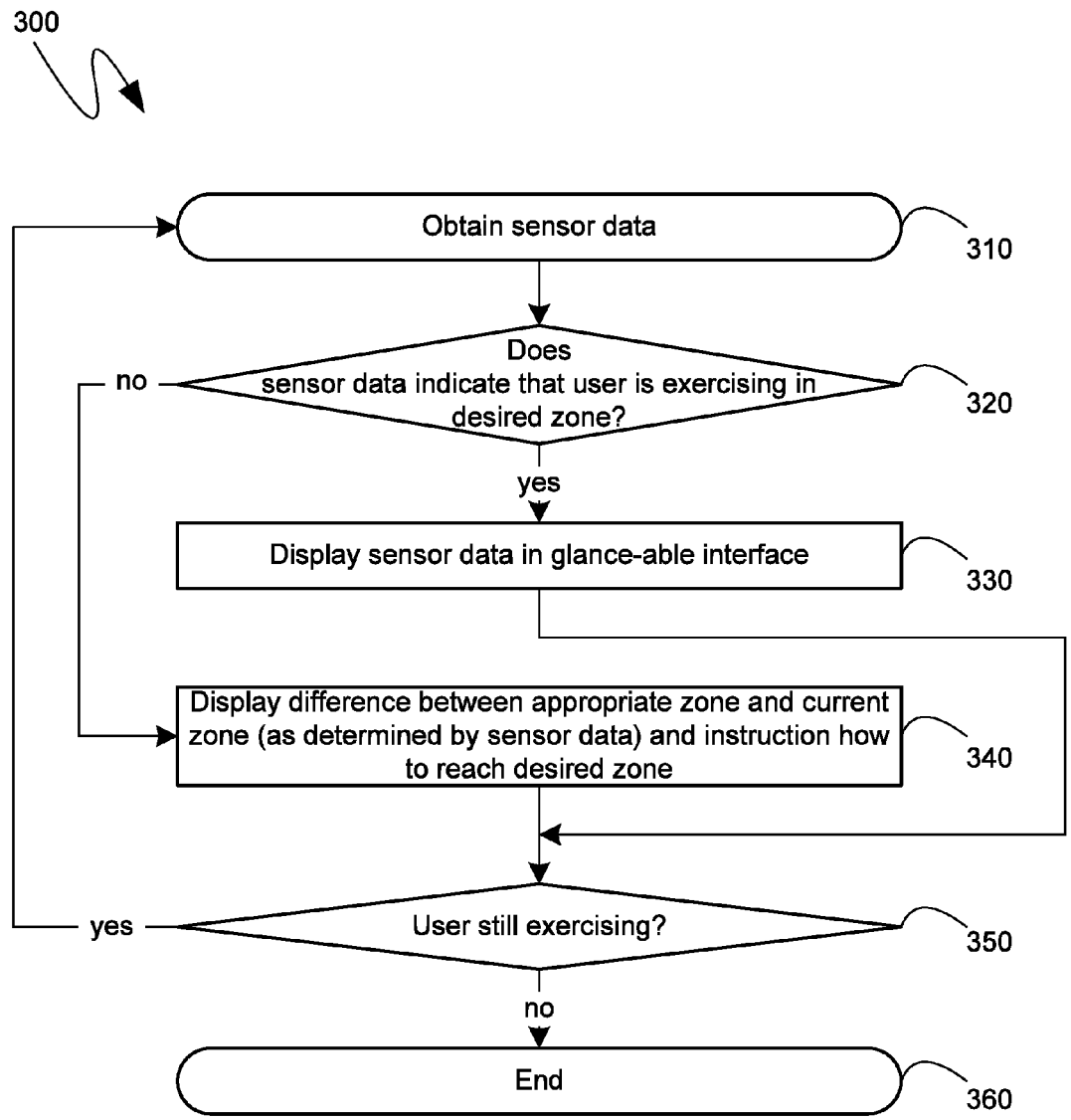
FIG. 4 is a flow diagram of an exemplary method of generating a portion of the glanceable interface.

FIG. 4 illustrates a flow diagram 300 describing an exemplary series of steps by which the glanceable interface 200, 250 and 270 can be generated. As shown, initially, at step 310, sensor data can be received, such as from the sensing module 90. Subsequently, a determination can be made, at step 320, as to whether the received data indicates that the user is exercising within their desired, or target, zone. If the user is exercising within their target zone, then, at step 330, the raw sensor data can be displayed in the glanceable interface, such as shown in the exemplary glanceable interface 270, comprising the goal information display 280, which displays only the measured beats-per-minute of the user's heart. Alternatively, if, at step 320, it is determined that the user is not exercising within their target zone, then, at step 340, a difference between the user's current exercise level and the user's target zone can be displayed, together with, optionally, instructions for the user to reach the target zone. For example, as shown in the exemplary glanceable interface 250, the goal information display 260 can display the discrepancy between the current beats-per-minute of the user's heart and the target beats-per-minute, together with an instruction for the user to increase their heart-rate in order to reach the target zone.

After either step 330 or 340 is performed, a check can be made, at step 350, to determine if the user is still active in their exercise session. Such a check can, for example, rely on sensor data or, alternatively, can be based on an exercise timer that can be pre-set by the user. If the user continues to exercise, then processing can return to step 310 while, if the user is found, at step 350, to have completed their exercise session, then, at step 360, the processing of the exemplary flow diagram 300 can end.

Returning to FIG. 3, the glanceable interface 200 can provide a user with directed motivation to maintain a particular level of exercise in accordance with the user's stated exercise goals. Additional motivation can be provided to the user via a virtual competition that can be displayed to the user through the competition information section 225 of the glanceable interface 200. In one embodiment, the virtual competition can be based on a score that can account for the maintenance of a competitor's exercise level within a target range based on that competitor's goals. In such a manner, the virtual competition need not reward raw strength or speed, but rather can reward ability of a competitor to maintain an exercise level appropriate for that competitor's goals. In such a manner, the virtual competition can provide a greater number of competitors with meaningful competition, and can, thereby, act to further motivate a user.

To provide an objective measure of a competitor's maintenance of their exercise level within a proscribed target range, a target-achievement-score can be generated that rewards exercise within the target range. The target-achievement-score can further penalize exercise outside of the target range. In one embodiment, the target-achievement-score can increase in value in proportion to the amount of time spent exercising within the target range, with the greatest increase in value being assigned to exercise levels that are centralized within the target zone. The target-achievement-score can still increase in value for time spent exercising outside of the target range, though the rate of increase can decrease as the competitor's exercise level further deviates from the target zone. In an alternative embodiment, no increase to the target-achievement-score can be provided by time spent exercising outside of a predetermined zone that can be either equal to the target zone, or can be greater than the target zone. In a further alternative embodiment, the target-achievement-score can be decreased for the time a competitor spends exercising outside of a predetermined zone that can, likewise, be either equal to the target zone or greater than the target zone.

The target-achievement-score can be based on any quantifiable exercise-related measure by which the user's exercise performance can, objectively, be determined. One common measure for exercise level is the heart rate of the individual performing the exercise. However, other similar measures exist and the below described formulas can be analogously adapted for such measures.

In one embodiment, the target-achievement-score can be based, at least in part, on the competitor's heart rate, and the ability of the competitor to maintain a target heart rate appropriate for that competitor's exercise-related goals. For example, the target-achievement-score at any point in time of an exercise session can be given by the following equation:

$$TargetAchievmentScore(x) = \frac{HeartRateAccuracy(x, HR) + ZoneAccuracy(x)}{2},$$

where "x" is the cumulative number of seconds of the exercise session up until the measured point in time.

As can be seen, in the described embodiment, the target-achievement-score can be a function of two variables; namely: "HeartRateAccuracy(x,HR)", which can represent the accuracy with which the competitor maintains a target heart rate, and "ZoneAccuracy(x)", which can represent the amount of time, up until the measured point in time, that the competitor maintained their heart rate within the target zone. In particular, the variable "ZoneAccuracy(x)" can be obtained from the following equation:

$$ZoneAccuracy(x) = \frac{SecondsInZone}{x},$$

while the variable "HeartRateAccuracy(x,HR)" can be obtained from the following equation:

$$HeartRateAccuracy(x, HR) = \frac{|fac(Hr) - \min(fac(HR_{rest}), fac(HR_{max}))|}{|HR_{target} - \min(fac(HR_{rest}), fac(HR_{max}))|},$$

where $$fac(HR) = HR_{target} + \left(\frac{1.5^{\frac{|HR_{target}-HR|}{\sqrt{2HR_{target}}}} - 1.5^{\frac{|HR_{target}-HR|}{\sqrt{2HR_{target}}}}}{2}\right).$$

As will be recognized by those skilled in the art, the variable "HeartRateAccuracy(x)" provides a hyperbolic relationship between the increase of the target-achievement-score and the closeness of the competitor's heart rate to the target heart rate.

Irrespective of the precise manner in which the target-achievement-score is determined, once data from one or more exercise sessions has been obtained, a target-achievement-score for each time increment of the exercise session can be computed. In one embodiment, such pre-computed target-achievement-score information can be used to inform the selection of appropriate competitors for a given user. For example, those competitors whose target-achievement-scores are closest to the user's most recent target-achievement-scores can be selected as the user's competitors by an automated process. In an alternative embodiment, to provide further motivation for the user, at least one competitor can be selected such that that competitor's target-achievement-scores are higher than the user's. If such a competitor is not among the closest competitors, then the automated selection of the user's competitors can replace one or more of the closest competitors with one or more of the competitors whose target-achievement-scores are higher than the user's.

Once the user's competitors have been selected, the user's target-achievement-score can be computed in real-time as the user engages in an exercise session, and can be compared to the target-achievement-scores of the user's competitors at an analogous point in time of their exercise sessions. In one embodiment, to account for exercise sessions of varying durations, the pre-computed target-achievement-scores of the user's competitors can be interpolated to synchronize with the user's indicated exercise duration. Thus, for example, if one of the user's competitors had engaged in an hour-long exercise session, and the user indicated an intention to engage in an exercise session of only a half-hour in length, then, for purposes of determining the user's rank among their competitors within the virtual competition, the competitor's target-achievement-scores can either be compressed into a duration of half the time, or every second target-achievement-score could be discarded. Similarly, if the user's competitors had engaged in a half-hour exercise session, and the user indicated that they intended to exercise for an hour, the competitors' target-achievement-scores for their half-hour session can be interpolated across an hour exercise session such that a meaningful comparison between the user's target-achievement-score and their competitors' target-achievement-scores can be made at each instant of the user's exercise session.

By comparing the user's real-time target-achievement-score to the pre-computed, and appropriately interpolated target-achievement-scores of the user's competitors, the user's rank within the virtual competition can be ascertained at any instant in time during their exercise session. Such a ranking can then be communicated to the user, such as through the competition information section 225 of the glanceable interface 200. Thus, as shown in FIG. 3, the users ranking can be prominently displayed, such as illustrated by exemplary competition information sections 265 and 285, and additional information, such as the names of the closest competitors, can likewise be displayed.

Figure 5A:
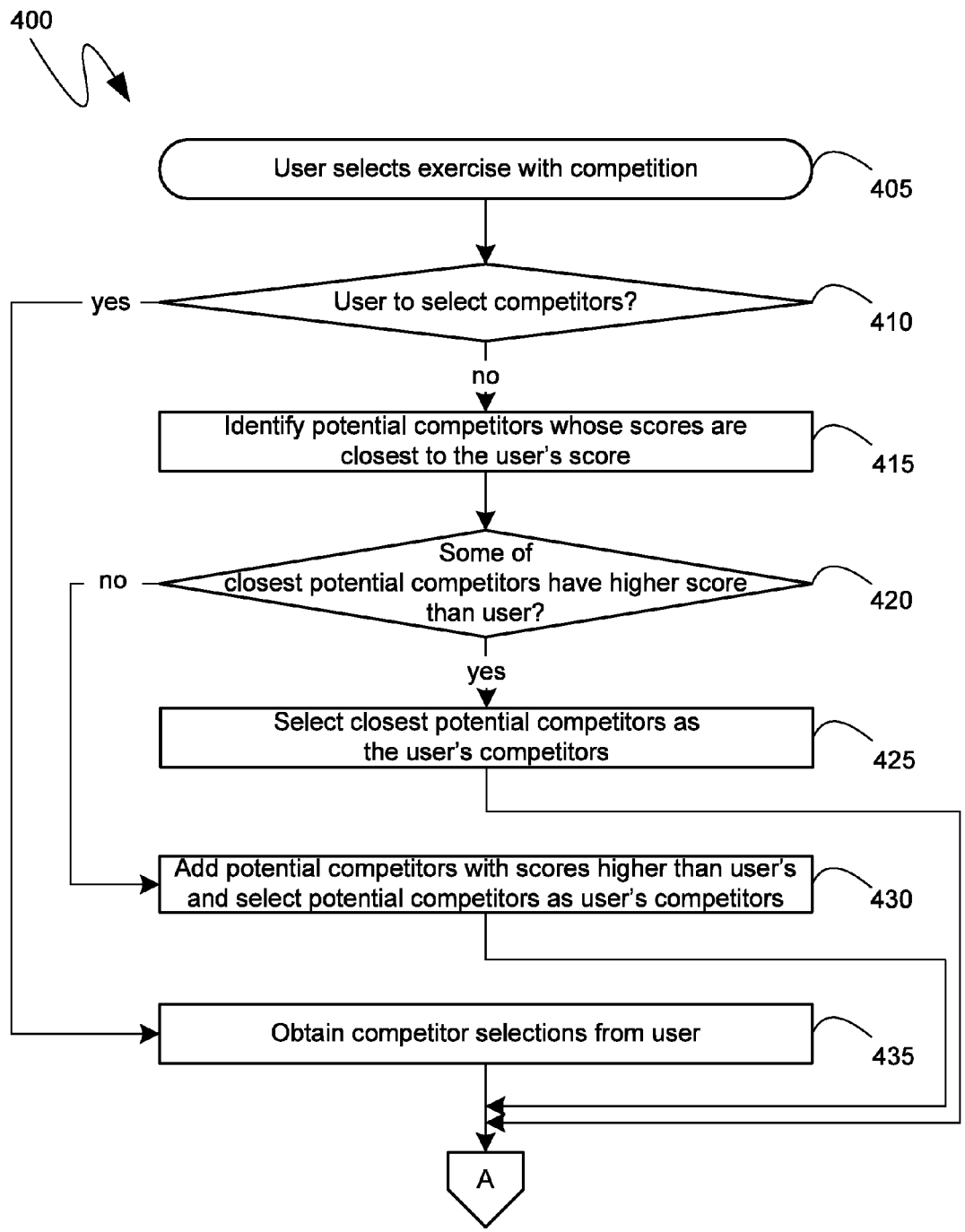
FIGS. 5*a* and 5*b* are a flow diagram of an exemplary method of providing virtual competition.
Figure 5B:
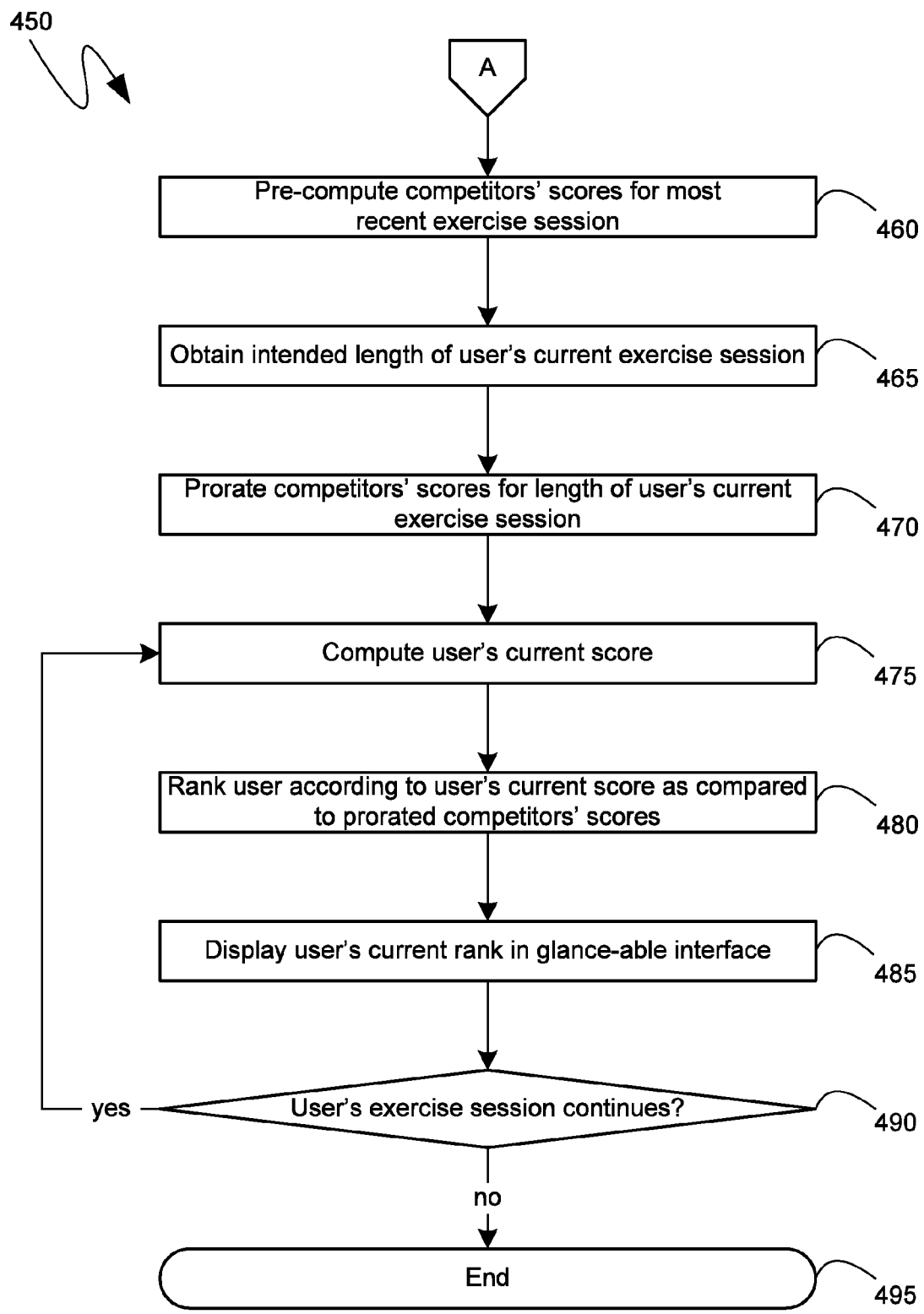

Turning to FIGS. 5*a* and 5*b*, a flow diagram comprising sequence of steps 400 and 450 is shown illustrating an exemplary implementation of virtual competition to increase a user's motivation to maintain a proper exercise level, given the user's predetermined exercise goals. Thus, as shown, at an initial step 405, the user can select to engage in virtual competition during their exercise session. Subsequently, at step 410, the user can select to automate the selection of competitors, or the user can manually select their competitors themselves. If the user selects the latter, then, at step 435, the user's selection of competitors can be received, such as through an appropriate user interface, and the process can continue with the sequence of steps 450, shown in FIG. 5*b*.

If the user, at step 410, enables the automatic selection of competitors, then, in one embodiment, an identification can be made, at step 415, of potential competitors whose target-achievement-scores throughout their exercise sessions are closest to the user's target-achievement-scores, such as during the user's most recent exercise session. As indicated, the potential competitors' target-achievement-scores throughout their exercise sessions can be pre-computed once the potential competitor's exercise data is obtained. At step 420, a determination can be made to ensure that at least some of the potential competitors have target-achievement-scores that are higher than the user's target-achievement-scores. If at least some of the potential competitors do have higher target-achievement-scores, then, at step 425, some or all of the potential competitors can be selected as the user's competitors and processing can continue with the sequence of steps 450, illustrated in FIG. 5*b*. However, if, at step 420, it is determined that none of the potential competitors have target-achievement-scores that are higher than the user's, potential competitors with higher target-achievement-scores can be added at step 430 and the user's competitors can then be selected from this modified set of potential competitors. In one embodiment, the potential competitor, from among those identified at step 415, whose target-achievement-score is furthest from the user's target-achievement-score, is removed and replaced, at step 430, by a potential competitor whose target-achievement-score is, from among those having higher target-achievement-scores, closest to the user's target-achievement-score.

As indicated previously, the target-achievement-scores throughout a competitor's exercise session can be determined once the data from the competitor's exercise session is received. Thus, while step 460 is illustrated as having a particular order within the flow diagram illustrated in FIGS. 5*a* and 5*b*, the pre-computation of target-achievement-scores referenced by step 460 can occur at any time.

When the user commences an exercise session, the intended length of the exercise session can be obtained from the user at step 465. The competitors' pre-computed target-achievement-scores can then be interpolated, at step 470, so as to match the intended length of the user's exercise session. Subsequently, at step 475, once the user has commenced their exercise session, a current target-achievement-score can be determined based on exercise-related data received from the sensing module 90. At each instant of time within the virtual competition, the user can be ranked, at step 480, based on the relative magnitude of the user's current target-achievement-score at that instant in time, as compared to the pre-computed and prorated competitors' target-achievement-scores at the same corresponding instant in time. The user's current rank can then be displayed, at step 485, as part of the glanceable interface 200.

A check can be made, at step 490, to ensure that the user's exercise session has completed. In one embodiment, the check at step 490 can be based on the user's intended length of their exercise session, as obtained at step 465. In an alternative embodiment, however, the check at step 490 can be based on the data received, such as from the sensing module 90, to determine if the user actually has ended their exercise session. If step 490 determines that the user's exercise session has ended, then the processing can end at step 495. Alternatively, if the determination at step 490 indicates that the user is continuing to exercise, then processing can return to step 475 to compute a new current target-achievement-score for the user.

In one embodiment, a user's exercise data, together with potential competitors' exercise data, can be stored on a remote computing device that can be accessed by the portable computing device 100, such as through the network 175. In such a case, the competitors for the virtual competition can be selected from a much greater, and, thus, potentially more applicable, pool of potential competitors. In addition, such a centralized storage of exercise data could enable a user to compete against acquaintances or family members despite being separated from such competitors by distance or time.

As can be seen from the above descriptions, a glanceable interface and virtual competition are provided via a computing device that a user can access while exercising so as to maintain and improve the user's motivation to exercise and to do so in an appropriate goal-oriented manner. In view of the many possible variations of the subject matter described herein, we claim as our invention all such embodiments as may come within the scope of the following claims and equivalents thereto.

We claim:

1. One or more computer-readable storage media comprising stored computer-executable instructions that, when executed by a computing device, cause the computing device to perform steps comprising:

receiving a user's exercise-related data from one or more sensors coupled to the user;

calculating a user's target-achievement-score during a user's exercise session, the user's target-achievement-score based on cumulative time of the user's exercise session up to a current time of the user's exercise session and factors comprising:

a user's heart rate during the user's exercise session as determined by reference to the user's exercise-related data, a user's target heart rate, a user's target heart rate zone defining upper and lower bounds for the user's target heart rate, a zone accuracy based on the cumulative time and a length of time during which the user's heart rate was maintained within the user's target heart rate zone during the user's exercise session up to the current time, and a heart rate accuracy with which the user's heart rate matched the user's target heart rate during the user's exercise session up to the current time, wherein the user's target-achievement-score increases for exercise within the user's target heart rate zone based on closeness of the user's heart rate to the user's target heart rate, and wherein the user's target-achievement-score penalizes exercise outside of the user's target heart rate zone;

determining a user's ranking relative to one or more virtual competitors based on a comparison between the user's target-achievement-score and each competitor's target-achievement-score at an analogous point in time of each competitor's exercise session; and providing, to the user, while the user is exercising, the user's ranking relative to the one or more virtual competitors.

2. The computer-readable storage media of claim 1 comprising further computer-executable instructions for selecting one or more virtual competitors from among potential virtual competitors based on a proximity between the virtual competitors' target-achievement-scores and a user's most recent target-achievement-score, wherein the virtual competitors' target-achievement-scores are pre-computed.

3. The computer-readable storage media of claim 2, wherein the selecting one or more virtual competitors comprises selecting at least one greater virtual competitor whose target-achievement-score is greater than the user's most recent target-achievement score.

4. The computer-readable storage media of claim 2, wherein the virtual competitors' target-achievement-scores are stored remotely from the user.

5. The computer-readable storage media of claim 1, wherein the comparison between the user's target-achievement-score and each competitor's target-achievement-score comprises interpolating each competitor's target-achievement-scores in accordance with that competitor's duration of exercise as compared to a user's anticipated duration of exercise.

6. The computer-readable storage media of claim 1, wherein the providing the user's ranking comprises providing the user's ranking in a prominent manner in a glanceable interface.

7. The computer-readable storage media of claim 6, wherein the glanceable interface further comprises: an indication of the difference between the user's exercise-related data and the user's target exercise level zone if the user's exercise-related data indicates that the user's exercise level is outside of the user's target exercise level zone.

8. The computer-readable storage media of claim 1, wherein the one or more sensors coupled to the user comprise an electrocardiogram sensor.

9. A computer-implemented method of providing exercise-oriented motivation to a user comprising the steps of:

receiving, at a computing device, a user's exercise-related data from one or more sensors coupled to the user;

calculating, at the computing device, a user's target-achievement-score during a user's exercise session, the user's target-achievement-score based on cumulative time of the user's exercise session up to a current time of the user's exercise session and factors comprising:

a user's heart rate during the user's exercise session as determined by reference to the user's exercise-related data, a user's target heart rate, a user's target heart rate zone defining upper and lower bounds for the user's target heart rate, a zone accuracy based on the cumulative time and a length of time during which the user's heart rate was maintained within the user's target heart rate zone during the user's exercise session up to the current time, and a heart rate accuracy with which the user's heart rate matched the user's target heart rate during the user's exercise session up to the current time, wherein the user's target-achievement-score increases for exercise within the user's target heart rate zone based on closeness of the user's heart rate to the user's target heart rate, and wherein the user's target-achievement-score penalizes exercise outside of the user's target heart rate zone;

determining a user's ranking relative to one or more virtual competitors based on a comparison between the user's target-achievement-score and each competitor's target-achievement-score at an analogous point in time of each competitor's exercise session; and providing, to the user, while the user is exercising, the user's ranking relative to the one or more virtual competitors on a display of the computing device.

10. The method of claim 9 further comprising:

selecting one or more virtual competitors from among potential virtual competitors based on a proximity between the virtual competitors' target-achievement-scores and a user's most recent target-achievement-score, wherein the virtual competitors' target-achievement-scores are pre-computed.

11. The method of claim 10, wherein the selecting one or more virtual competitors comprises selecting at least one greater virtual competitor whose target-achievement-score is greater than the user's most recent target-achievement score.

12. The method of claim 9, wherein the comparison between the user's target-achievement-score and each competitor's target-achievement-score comprises prorating each competitor's target-achievement-scores in accordance with that competitor's duration of exercise as compared to a user's anticipated duration of exercise.

13. The method of claim 9, wherein the user's raking is provided via a glanceable interface, the glanceable interface further comprising: an indication of the difference between the user's exercise-related data and the user's target exercise level zone if the user's exercise-related data indicates that the user's exercise level is outside of the user's target exercise level zone; and an indication of the user's exercise-related data if the user's exercise-related data indicates that the user's exercise level matches a user's target exercise level, wherein the user's target exercise level is associated with the user's target exercise level zone.

14. The method of claim 13, wherein the glanceable interface further comprises an instruction to the user directed to modifying the user's exercise level to conform to the user's target exercise level zone if the user's exercise-related data indicates that a user's exercise level is outside of the user's target exercise level zone.

15. The computer-readable storage media of claim 1 wherein the user's ranking relative to the one or more virtual competitors is not determined based on speed of the user or speed of the one or more virtual competitors.

16. The computer-readable storage media of claim 1 wherein the heart rate accuracy provides a hyperbolic relationship between an increase of the user's target-achievement-score and the closeness of the user's heart rate to the user's target heart rate.

17. The computer-readable storage media of claim 1 wherein the user's target-achievement-score, TargetAchievementScore(x), is given by:

$$TargetAchievmentScore(x) = \frac{HeartRateAccuracy(x, HR) + ZoneAccuracy(x)}{2},$$

where:
"x" is cumulative number of seconds of the user's exercise session up to the current time,
"HR" is the user's heart rate, $$ZoneAccuracy(x) = \frac{SecondsInZone}{x},$$

SecondsInZone is number of seconds that the user's heart rate was maintained within the user's target heart rate zone during the user's exercise session up to the current time, $$HeartRateAccuracy(x, HR) = \frac{|fac(HR) - \min(fac(HR_{rest}), fac(HR_{max}))|}{|HR_{target} - \min(fac(HR_{rest}), fac(HR_{max}))|},$$

$$fac(HR) = HR_{target} + \left( \frac{1.5^{\sqrt{\frac{|HR_{target} - HR|}{2HR_{target}}}} - 1.5^{\sqrt{\frac{|HR_{target} - HR|}{2HR_{target}}}}}{2} \right),$$

"$HR_{target}$" is the user's target heart rate, and
"$HR_{rest}$" is the user's resting heart rate.

18. The method of claim 9, wherein the user's ranking relative to the one or more virtual competitors is not determined based on speed of the user or speed of the one or more virtual competitors.

19. The method of claim 9, wherein the heart rate accuracy provides a hyperbolic relationship between an increase of the user's target-achievement-score and the closeness of the user's heart rate to the user's target heart rate.

20. The method of claim 9, wherein the user's target-achievement-score, TargetAchievementScore(x), is given by:

$$TargetAchievmentScore(x) = \frac{HeartRateAccuracy(x, HR) + ZoneAccuracy(x)}{2},$$

where
"x" is cumulative number of seconds of the user's exercise session up to the current time,
"HR" is the user's heart rate, $$ZoneAccuracy(x) = \frac{SecondsInZone}{x},$$

SecondsInZone is number of seconds that the user's heart rate was maintained within the user's target heart rate zone during the user's exercise session up to the current time, $$HeartRateAccuracy(x, HR) = \frac{|fac(HR) - \min(fac(HR_{rest}), fac(HR_{max}))|}{|HR_{target} - \min(fac(HR_{rest}), fac(HR_{max}))|},$$

$$fac(HR) = HR_{target} + \left( \frac{1.5^{\sqrt{\frac{|HR_{target} - HR|}{2HR_{target}}}} - 1.5^{\sqrt{\frac{|HR_{target} - HR|}{2HR_{target}}}}}{2} \right),$$

"$HR_{target}$" is the user's target heart rate, and
"$HR_{rest}$" is the user's resting heart rate.

* * * * *